(12) United States Patent
Simonsen

(10) Patent No.: US 12,082,869 B2
(45) Date of Patent: Sep. 10, 2024

(54) ELECTRODE FOR AN ELECTROSURGICAL PENCIL AND A METHOD OF MAKING AN ELECTRODE

(71) Applicant: Stryker European Operations Limited, County Cork (IE)

(72) Inventor: Jesper Schantz Simonsen, Jyderup (DK)

(73) Assignee: Stryker European Operations Limited, Cork (IE)

( * ) Notice: Subject to any disclaimer, the term of this patent is extended or adjusted under 35 U.S.C. 154(b) by 456 days.

(21) Appl. No.: 16/649,618

(22) PCT Filed: Oct. 19, 2018

(86) PCT No.: PCT/EP2018/077430
§ 371 (c)(1),
(2) Date: Mar. 20, 2020

(87) PCT Pub. No.: WO2019/072819
PCT Pub. Date: Apr. 18, 2019

(65) Prior Publication Data
US 2020/0268437 A1     Aug. 27, 2020

(30) Foreign Application Priority Data
Oct. 9, 2017 (EP) ..................... 17195450

(51) Int. Cl.
*A61B 18/14* (2006.01)
*A61B 17/00* (2006.01)
*A61B 18/00* (2006.01)

(52) U.S. Cl.
CPC .............. *A61B 18/1402* (2013.01); *A61B 2017/00526* (2013.01); *A61B 2018/00107* (2013.01);
(Continued)

(58) Field of Classification Search
CPC .......... A61B 2017/00526; A61B 2018/00107; A61B 2018/0013; A61B 2018/00196;
(Continued)

(56) References Cited

U.S. PATENT DOCUMENTS 5,380,320 A      1/1995  Morris
5,702,387 A  *  12/1997  Arts ................... A61B 18/1402
                                                606/49
(Continued)

FOREIGN PATENT DOCUMENTS

EP      0 779 061 A2    6/1997
EP      1 259 183 B1   11/2002
(Continued)

OTHER PUBLICATIONS

International Search Report dated Dec. 7, 2018, issued in connection with International Application No. PCT/EP2018/077430, filed on Oct. 9, 2018, 2 pages.
(Continued)

*Primary Examiner* — Daniel W Fowler
*Assistant Examiner* — Bradford C. Blaise
(74) *Attorney, Agent, or Firm* — McDonnell Boehnen Hulbert & Berghoff LLP

(57) ABSTRACT

An electrode for an electrosurgical pencil, the electrode comprising an elongated body made of a conductive material and extending in an axial direction from a proximal end to a distal end, the proximal end configured for engaging the electrosurgical pencil and the distal end forming a blade configured for cutting or coagulation of tissue by electrosurgical energy received from the pencil, the blade being defined by two main surface portions on opposite sides of an axially extending intermediate plane and joined by an edge extending through the intermediate plane. To concentrate electrical energy at the edge and thereby facilitate a more (Continued)

precise cutting and less burnt tissue sticking to the electrode, the main surface portions has a first surface roughness, the edge has a second surface roughness being lower than the first surface roughness, and at least the main surface portions are covered by a surface coating comprising silicone.

20 Claims, 3 Drawing Sheets

(52) U.S. Cl.
CPC .............. *A61B 2018/0013* (2013.01); *A61B 2018/00607* (2013.01); *A61B 2018/1412* (2013.01)

(58) Field of Classification Search
CPC ........... A61B 2018/00589; A61B 2018/00601; A61B 2018/00607; A61B 2018/00958; A61B 2018/1412; A61B 2018/1475; A61B 18/1402; A61B 18/1477
See application file for complete search history.

(56) References Cited

U.S. PATENT DOCUMENTS

| | | | |
|---|---|---|---|
| 5,713,895 A * | 2/1998 | Lontine | A61B 18/1402 606/49 |
| 5,800,427 A * | 9/1998 | Zamba | A61B 18/1402 606/39 |
| 6,132,427 A | 10/2000 | Jones et al. | |
| 6,139,547 A | 10/2000 | Lontine et al. | |
| 6,533,781 B2 * | 3/2003 | Heim | A61B 18/14 606/49 |
| 2001/0031964 A1 * | 10/2001 | Gentelia | A61B 18/1402 606/45 |
| 2011/0184410 A1 * | 7/2011 | Greep | A61B 18/1402 606/41 |
| 2013/0197549 A1 * | 8/2013 | Kato | A61B 17/06066 606/167 |

FOREIGN PATENT DOCUMENTS

| | | |
|---|---|---|
| EP | 1 330 990 A1 | 7/2003 |
| JP | 2010284439 A | 12/2010 |
| WO | 2011/090507 A1 | 7/2011 |
| WO | 2016/051918 A1 | 4/2016 |

OTHER PUBLICATIONS

Written Opinion dated Dec. 7, 2018, issued in connection with International Application No. PCT/EP2018/077430, filed on Oct. 9, 2018, 6 pages.

* cited by examiner

ELECTRODE FOR AN ELECTROSURGICAL PENCIL AND A METHOD OF MAKING AN ELECTRODE

CROSS REFERENCE TO RELATED APPLICATIONS

This application is a U.S. National Phase Application under 35 U.S.C. § 371 of International Application No. PCT/EP2018/077430, filed Oct. 9, 2018, which claims the benefit of European Patent Application No. 17195450.6, filed Oct. 9, 2017, the disclosures of each of which are entirely incorporated herein by reference.

The present disclosure relates to an electrosurgical pencil and an electrode for an electrosurgical pencil for cutting or coagulation of tissue. The pencil and electrode has a particular structure which increases the precision particularly in a tissue cutting process.

BACKGROUND OF THE INVENTION

Electro-Surgical (ES) pencils are used in surgery, typically for cutting tissue and/or for coagulating blood. An ES pencil usually comprises a hand-piece into which electrodes of many different shapes and sizes may be placed. The electrode is supplied with a high frequency, typically Radio Frequency (RF), alternating current signal by an RF source. The RF source is typically called the Electro-Surgical Unit or ESU.

By varying the voltage and/or the frequency of the RF signal supplied by the ESU, the electrode can be used in different modes. Two common modes are a cutting mode and a coagulating mode.

During a surgical procedure, tissue may adhere to the electrode and thus change the shape of the electrode. Particularly, this may impair the ability to make thin incisions and impair the quality and speed of the medical procedure. Particularly, that part of the electrode which is in contact with tissue, herein referred to as the working surface, is subject to high temperatures during use. The high temperature causes the tissues to stick to the electrode. At very high temperatures the tissue may even become charred. Build-up of charred tissue on the electrode reduces the transfer of energy and makes precise surgery difficult. Further, it is sometimes experienced that the electrode sticks to the tissue and thereby prevents smooth movement of the electrode through the tissue. Additionally, solid binding of low friction coatings onto the conductive electrode is sometimes problematic.

SUMMARY OF THE INVENTION

To overcome problems with operating the existing pencils, and particularly to improve the ability to make precise and thin incisions, a new electro-surgical pencil electrode, a method of making such an electrode, and pencil with such an electrode is provided.

The electrode comprises an elongated body made of a conductive material and extending in an axial direction from a proximal end to a distal end, the proximal end configured for engaging the electrosurgical pencil and the distal end forming a blade configured for cutting or coagulation of tissue by electrosurgical energy received from the pencil.

The blade is defined by two main surface portions on opposite sides of an intermediate plane. The main surface portions are joined by an edge. The intermediate plane is introduced as a virtual plane, i.e. it is not formally to be recognized on the electrode, but introduced herein for defining the main surface portions and the edge.

The transition between each main surface portion and the edge may particularly be defined by a bend in a curve extending from the main surfaces into the edge, i.e. the curve forms a bend which can be recognised as an increased slope of the tangent to that curve. The transition is herein referred to as corner between the main surface portion and edge.

The edge may constitute three edge portions, i.e. two extending in the axial direction, referred to herein as "axial edges", and one terminating the blade in the distal end, referred to herein as "tip edge".

With this definition, the smooth part may be constituted by at least a part of the axial edges, and the tip edge may either have the same or a larger roughness than the axial edges.

The main surface portions, or at least one of them, have a first surface roughness, the smooth-part of the edge has a second surface roughness being lower than the first surface roughness, and at least the main surface portions are covered by a surface coating e.g. comprising silicone.

The smooth part of the edge may constitute the entire edge, i.e. the axial edges and the tip edge, or the smooth part may constitute at least one of the tip edge and the axial edge, e.g. only at least one of the axial edges or only the tip edge. In one particular embodiment, the smooth-part is constituted by both axial edges but not by the tip edge.

Due to the difference in surface roughness, different surface characteristics can be obtained for different parts of the electrode. Particularly, it may be easier to bond a surface coating to a rough surface due to the increased surface area and the ability of the coating to grip the uneven surface. On the contrary, the less rough surface does not facilitate the same bonding of coating, but the smoothness of the surface may facilitate easy sliding of an uncoated electrode through the tissue. Due to the smoothness, the less rough surface can be un-coated which improves the ability to conduct electrical current, and the resulting electrode facilitates a precise cut with a sufficient electrical current and a smooth, low-frictional, movement through the tissue.

The difference in surface roughness may provide an improved bonding of the coating to the main surface portions compared to the smooth-part of the edge. Accordingly, the invention may provide a coating which is strongly bonded to the main surface portions to provide a superior anti-stick surface with very little risk of char build-up. The less rough smooth-part of the edge can provide superior conductivity, and simultaneously it may provide good sliding of the edge through the tissue. Accordingly, the electrode according to the present disclosure enables precise, fine cutting with reduced char build-up.

At least the smooth-part of the edge or the entire edge may be non-coated meaning that the conductive material of the electrode is exposed completely thereby increasing conductivity further. By not coating the smooth-part of the edge, the conductivity from the smooth-part may be increased as compared to the conductivity from the coated main surface portion. Accordingly, the energy can be concentrated at that part of the edge. This effect can be increased by use of an electrically isolating coating or a coating have a much lower electrical conductivity than the conductive material of the body. The conductivity may e.g. be less than one tenth of the conductivity of the conductive material.

The main surface portions may have a large area when compared to the area of the edge. The surface coating may have a friction which is lower than the friction of the smooth part of the edge. This may allow a very low resistance against sliding against the typically large area of the main surface portions as compared to the typically smaller surface area of the edge.

The surface coating may comprise silicone or other friction reducing compositions, e.g. PTFE, and it may be applied with a non-even coating thickness. The concentration of energy to the edge of the electrode can be further increased by a surface coating having a non-even coating thickness. Particularly, the coating thickness may be gradually or stepwise reduced from a relatively large thickness in the middle of the main surface portions towards a thin or even completely eliminated surface coating at the corner or edge.

The thickness of the surface coating may be in the range of 0-350 μm, such as below 250 μm or below 150 μm and the surface coating may particularly comprise silicone, e.g. Silpuran from Wacker Chemie AG, Germany. Particularly, the selected coating may be configured for an ignition temperature up to 450° C.

By roughness is herein meant a surface texture quantified by the deviations in the direction of the normal vector of a real surface from its ideal form. If these deviations are large, the surface is herein defined as being rough. If the deviations are small, the surface is defined as being less rough or smooth. Roughness can be measured by manual comparison against a surface roughness comparator which is typically a small sample of known surface roughness. Surface profile and thus roughness measurement could also be made with a profilometer, e.g. of the contact variety with a diamond stylus, or they could be optical, e.g. with a light interferometer or laser scanning confocal microscope. There are different ways of expressing roughness and $R_a$ is commonly chosen.

A particular effect is achievable by having a large variation between the first and the second roughness. The second roughness may particularly be less than half of the first surface roughness when measured e.g. in the unit $R_a$. In absolute terms, the first roughness may preferably be in the range of 2.0-4.0 Ra, e.g. 2.4-3.4 $R_a$, and the second roughness may be in the range 0.5-1.5, e.g. less than 1 $R_a$.

In one embodiment, the edge is completely uncovered. To improve the precision further and provide even thinner incisions, it may, however, be an advantage to provide an edge which is at least partly covered by the surface coating. In one embodiment, a first part of the edge is covered by the surface coating and a second part of the edge is uncovered. The second part may constitute at least one corner between an oblong edge part extending in the axial direction and an end part extending transverse to the axial direction and terminating the electrode in the distal end. Particularly, both corners at the transition to the end part may be uncovered to thereby expose the metal at these corners. Additionally, these uncovered corners may be sharpened to provide thin and sharp uncovered edges by which the surgeon may cut precisely.

The corner forming a transition between a main surface portion and the axial edges are referred to as "axial corner", and the corner forming a transition between a main surface portion and the tip edge is referred to as "tip corner". With this definition, at least one of the tip corner and axial corners may be uncoated and in one embodiment, both the tip corner and axial corners are uncoated. At least one of the axial and tip corners may have a radius of curvature below 2 mm. or even below 1 mm to thereby further increase the concentration of energy and optionally to prevent coating to stick to the edge.

The surface coating on the covered part of the edge may be in the range of 0-150 μm and the surface coating may be of the same composition as the surface coating on the main surface portions. In one embodiment, the surface coating of the covered part of the edge is thicker than the surface coating on the main surface portions, e.g. in the range of 1.1-3 times the thickness of the coating on the main surface portions.

In one embodiment, the surface coating on the coated part of the edge is different from the surface coating on the main surface portions.

The first part of the edge may have a first edge surface roughness and the second part of the edge may have a second edge surface roughness being lower than the first edge surface roughness. A particular effect is achievable by having a large variation between the first and the second edge roughness. The second edge surface roughness may particularly be less than half of the first edge surface roughness when measured e.g. in the unit $R_a$. In absolute terms, the first edge surface roughness may be in the range of 0.5-1.0 $R_a$, and the second edge surface roughness may be in the range of 0.1-0.5 $R_a$.

In one embodiment, the second part of the edge is polished to obtain a very low roughness.

The edge may have a height defining a distance between the main surface portions being in the range of 0.3-0.7 mm, e.g. in the size of 0.5 mm. The main surface portions may each have an area in the range of 30-50 square millimetres, e.g. in the size of 40 square millimetres, and they may particularly be of identical size. The ratio between the area of the main surface portions and the area of the edge may be at least 1:5 meaning that the surfaces have a total area of at least 5 times the area of the edge.

The conductive material may be a stainless steel material, e.g. steel 1.4305, popularly known as grade 303 stainless steel, or it may be of other austenitic grades which are machineable, e.g. grades containing Sulphur.

In a second aspect, the disclosure provides a method of making an electrode for an electrosurgical pencil, the electrode comprising an elongated body made of a conductive material and extending in an axial direction from a proximal end to a distal end, the proximal end configured for engaging the electrosurgical pencil and the distal end forming a blade configured for cutting or coagulation of tissue by electrosurgical energy received from the pencil, the method comprising:

providing the elongated body with two main surface portions on opposite sides of an axially extending intermediate plane and joined by an edge extending through the intermediate plane, roughening the two main surface portions without roughening the edge;

coating at least the two main surface portions with a surface coating comprising silicone.

The roughening of the two main surface portions could be carried out by a blasting process, e.g. sand blasting, by use of sand paper etc., or by chemical treatment by use of acid etc. e.g. by sand blasting with abrasive sand having a grain size of 0.125-0.25 mm in diameter.

In the process of roughening the main surface portions, the edge could be masked to prevent roughening during the blasting, sanding, or chemical treatment. The unmasked surfaces are roughened and then dipped in a liquid silicone. In one process, the dipping is carried out after removing the masking such that both the main surface portions and the edge are covered by silicone. Alternatively, the masking remains until after the dipping. This will enable an uncoated or only partly coated edge.

To finalize the coating process, the electrode may be heated, or simply allowed to cure at room temperature.

In one embodiment, the masking is removed from selected areas of the edge to thereby leave only selected areas of the edge uncovered.

As an alternative to the masking of the edge, the non-roughened edge could be obtained by polishing the edges after the roughening of the main surface portions. The polishing could be carried out by sanding with grain 3000 sand paper and subsequent use of abrasive polishing paste. Alternatively, the edges could be chemically polished. In one embodiment, only selected areas of the edge is polished, leaving the edge with two different roughness, i.e. a first part having a first edge surface roughness and a second part having a second edge surface roughness being lower than the first edge surface roughness. The first part of the edge could be coated with the surface coating and the second part of the edge could be left uncoated or it could even be polished after the coating process to ensure a completely uncoated an clean part of the edge with superior properties relative to conduction of electrical current to tissue.

The second part could be sharpened further, e.g. by an abrasive process, by milling, or by any similar kind of mechanical material removal process. In this process, at least one sharp corner of the edge could be formed in the area between an edge part extending in the longitudinal direction and an edge part terminating the electrode in the distal end.

In a third aspect, the disclosure relates to an electrosurgical pencil with an electrode as described above.

In further aspects, the disclosure relates to methods of using the pencil and electrode during surgery.

Any of the second, third, and further aspects, may include any of the features mentioned for the first aspect of the invention.

LIST OF DRAWINGS

FIG. 1 illustrates a pencil with an electrode;
FIG. 2 illustrates in a perspective view, the electrode for the pencil;
FIG. 3 illustrates a cross section of the blade part of the electrode;
FIGS. 4-7 illustrate different views of the electrode blade seen from the distal end of the electrode;
FIG. 8 illustrates in top view of the electrode; and
FIG. 9 illustrates in a diagram, the process of making the electrode.

DESCRIPTION OF EMBODIMENTS

FIG. 1 shows a perspective view of the pencil 1 for cutting and/or coagulating tissue of a patient during surgery by application of electrical energy supplied from an electrosurgical generator (not shown). The pencil 1 comprises a hollow body 2 extending in an axial direction, an electrode 3 which can be used for cutting and/or coagulation. A switch 4 is provided for switching between different settings of the generator. In the disclosed embodiment, the switch is a rocker switch by which a surgeon can switch between a power mode for cutting and a power mode for coagulation by pressing one of the two ends of the switch 4. The axial direction is illustrated by the arrow 5.

The body 2 has a substantially semi-circular or circular cross-section to make handling easier, not least with respect to rotation of the pencil about an axis defining the longest extend of the pencil.

FIG. 2 illustrates an enlarged view of the electrode 3 without the pencil. The electrode comprises an elongated body made of a conductive material extending in the axial direction from a proximal end 6 to a distal end 7.

A proximal part forms an elongated plug 8 with a circular cross section and matches into a corresponding socket located in the distal end 9 of the pencil.

A working area 10 forms a blade which is configured for cutting or coagulation of tissue by the electrosurgical energy from the pencil. At least a part of the working area is coated with a slip surface reducing build up of eschar on the blade.

FIG. 3 illustrates the blade in a cross section perpendicular to the axial direction. The working area forms two main surface portions 11, 12 on opposite sides of an intermediate plane illustrated by the dotted line 13. The two main surface portions are joined by an edge 14 extending through the intermediate plane 13.

A surface coating is applied to the main surface portions but not to the edge. The surface coating has a thickness indicated by t. The applied coating is a non-slump to self-levelling silicone rubber formulation which cures at room temperature by moisture and thereby provides an elastomer with good mechanical properties. The selected coating is Silpuran 4200. The coating thickness t could be e.g. be 0.10±0.05 mm. in an area extending from 2.5 to 16 mm from the distal end.

FIGS. 4-7 illustrate different views of the blade seen from the distal end.

In FIG. 4 where only the blade is seen from the distal end, it is clearly illustrated that the electrode, in one embodiment forms two axial edges 15, 16 extending in the axial direction, and one tip edge 17 terminating the blade in the distal end. An axial corner 18 forms a transition between a main surface portion 19, and the axial edges and a tip corner form a transition between a main surface portion and the tip edge. The tip corner and/or one of the axial corners are uncoated to provide better conduction of an electrical current.

FIG. 5 illustrates the blade and the proximal plug part 20 of the electrode configured for engaging the pencil.

FIG. 6 illustrates only the blade. In this view, the uneven coating thickness of the coating 21 is clearly illustrated. The coating is thin near the corner 22, and there is no coating on the edge 23. The corner 22 is sharp, meaning that the radius of curvature is less than 2 mm. or even less than 1 mm or less than 0.5 mm.

Figure 1:
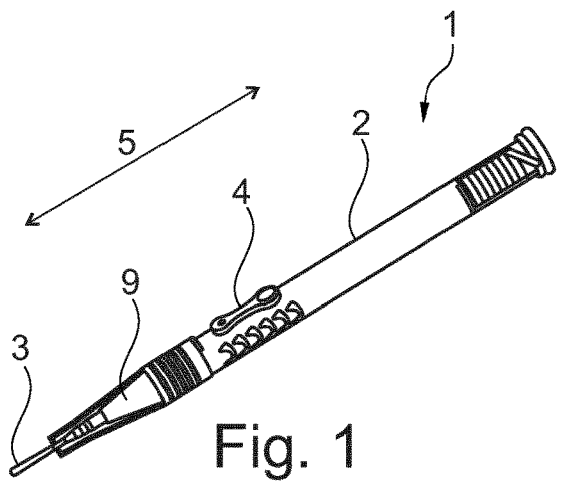
Figure 2:
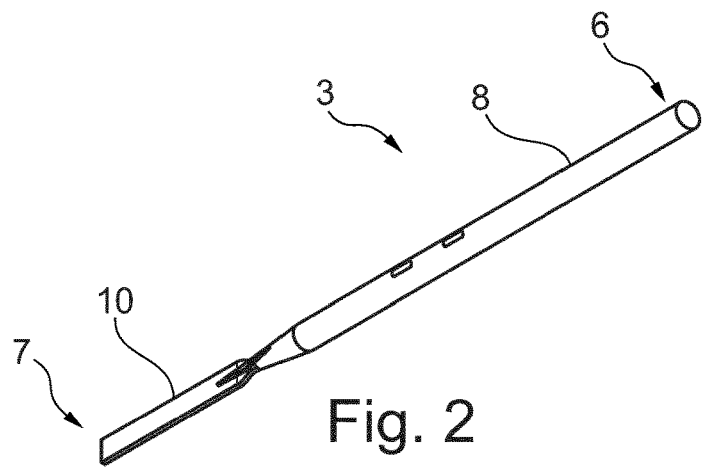
Figure 3:
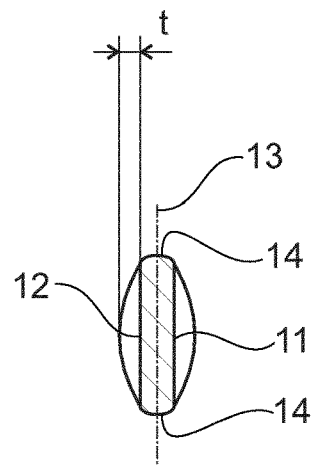
Figure 4:
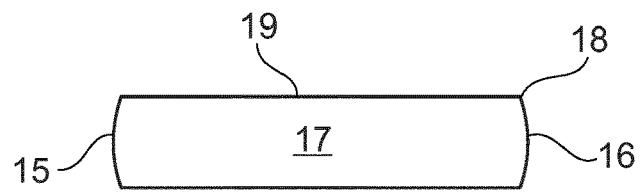
Figure 5:
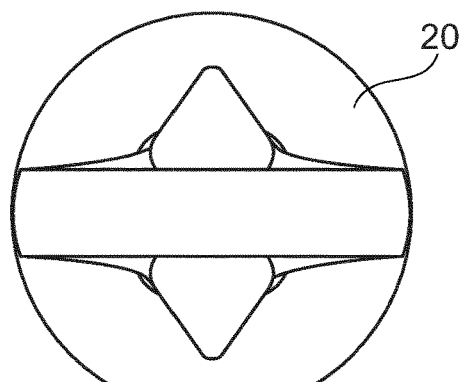
Figure 6:
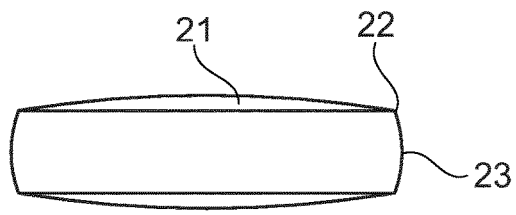
Figure 7:
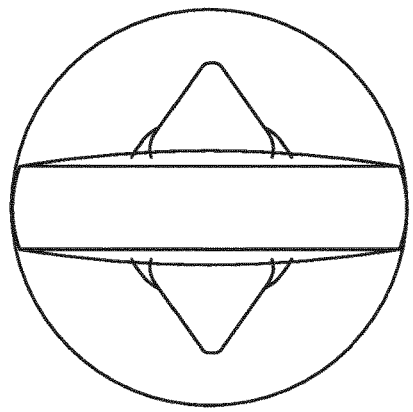
FIG. 7 illustrates FIG. 6 with the plug part 20.
Figure 8:
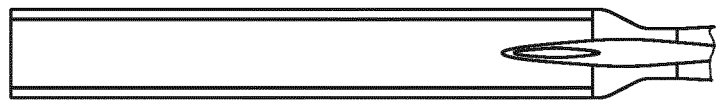
FIG. 8 illustrates a top view of the working area of the electrode.
Figure 9:
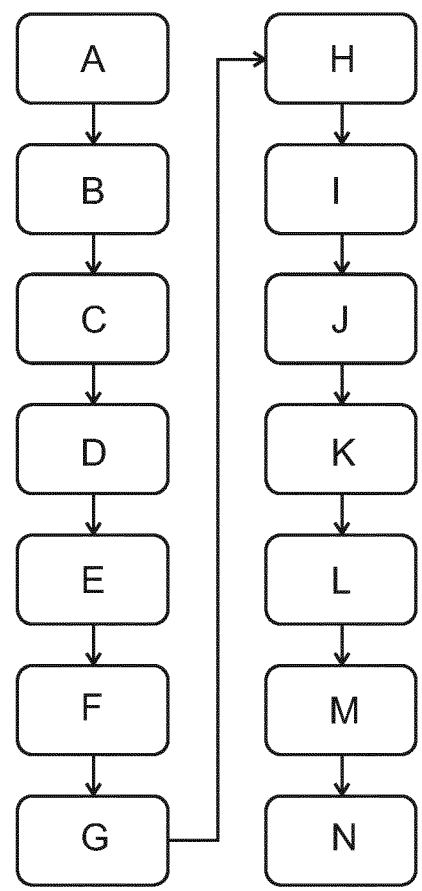

The process is illustrated in FIG. 9. In this diagram, the following details apply relative to the processes:

A: A metal rod having the desired shape with a working area forming two main surface portions joined with an edge is received;

B: the surface of the rod is cleaned, e.g. in alcohol. This step could be eliminated depending on the condition of the rod which is received;

C: high temperature, e.g. 400° C., could be applied for further degreasing;

D: the rod is cooled to ambient temperature;

E: the main surface portions are sandblasted to $R_a 2.9\pm0.5$ e.g. using sand with a diameter d being in the range of 0.125 and 0.25; in this process, the edge is not sandblasted;

F: the rod is treated at high temperatures in the range of 400° C., e.g. in 120 minutes;

G: the rod is cooled to ambient temperature;

H: the rod is oriented with the working area pointing downwards relative to gravity;

I: the working area is dipped in a liquid silicone polymer;

J: the working area is withdrawn from the liquid silicone polymer;

K: the working area is allowed to drip in an orientation where the working area remains downwards, or where the axial direction is horizontal;

L: the coating is mechanically removed from the edge;

M: the orientation is inverted to bring the working portion pointing upwards relative to gravity;

N: The silicone polymer is cured at ambient temperature for at least eight hours.

In step L, the removal of coating from the edge may be carried out in a process where the roughness at the edge is reduced, e.g. to a level close to zero. This may facilitate easier sliding of the electrode against the tissue surface and thus increase the ability to make fine incisions.

LIST OF EMBODIMENTS

1. An electrode for an electrosurgical pencil, the electrode comprising an elongated body made of a conductive material and extending in an axial direction from a proximal end to a distal end, the proximal end configured for engaging the electrosurgical pencil and the distal end forming a blade configured for cutting or coagulation of tissue by electrosurgical energy received from the pencil, the blade being defined by two main surface portions on opposite sides of an intermediate plane and joined by an edge extending through the intermediate plane, wherein the edge comprises a smooth-part, and wherein the main surface portions have a first surface roughness, the smooth-part of the edge has a second surface roughness being lower than the first surface roughness, and where at least the main surface portions are covered by a surface coating 2. An electrode according to embodiment 1, wherein the edge forms two axial edges extending in the axial direction, and one tip edge terminating the blade in the distal end, wherein the smooth part is constituted by at least a part of the axial edges, and wherein the tip edge has a larger roughness than the smooth part.

3. An electrode according to embodiment 1, wherein the edge forms two axial edges extending in the axial direction, and one tip edge terminating the blade in the distal end, wherein the smooth part is constituted by at least a part of the axial edges and a part of the tip edge.

4. An electrode according to any of the preceding embodiments, wherein the surface coating has a friction which is lower than the friction of the smooth part of the edge.

5. An electrode according to any of the preceding embodiments, wherein the surface coating comprises silicone.

6. An electrode according to any of the preceding embodiments, wherein the surface coating has a non-even coating thickness.

7. An electrode according to any of the preceding embodiments, wherein the second roughness $R_a$ is less than half of the first surface roughness $R_a$.

8. An electrode according to any of the preceding embodiments, wherein the edge is at least partly un-covered by the surface coating.

9. An electrode according to embodiment 8, wherein a first part of the edge is covered by the surface coating and a second part of the edge is uncovered.

10. An electrode according to embodiment 9, wherein the second part of the edge is the smooth-part of the edge.

11. An electrode according to embodiment 9 or 10, wherein the first part has a first edge surface roughness and the second part has a second edge surface roughness being lower than the first edge surface roughness.

12. An electrode according to any of the proceeding embodiments, wherein the edge forms two axial edges extending in the axial direction, and one tip edge terminating the blade in the distal end, and wherein an axial corner forms a transition between a main surface portion and the axial edges and a tip corner forms a transition between a main surface portion and the tip edge, wherein at least one of the tip corner and axial corners are uncoated.

13. An electrode according to any of the preceding embodiments, wherein the edge forms two axial edges extending in the axial direction, and one tip edge terminating the blade in the distal end, and wherein an axial corner forms a transition between a main surface portion and the axial edges and a tip corner forms a transition between a main surface portion and the tip edge, wherein both the tip corner and the axial corners are uncoated.

14. A method of making an electrode for an electrosurgical pencil, the electrode comprising an elongated body made of a conductive material and extending in an axial direction from a proximal end to a distal end, the proximal end configured for engaging the electrosurgical pencil and the distal end forming a blade configured for cutting or coagulation of tissue by electrosurgical energy received from the pencil, the method comprising:
    providing the elongated body with two main surface portions on opposite sides of an axially extending intermediate plane and joined by an edge extending through the intermediate plane,
    roughening the two main surface portions without roughening the edge;
    coating at least the two main surface portions with a surface coating comprising silicone.

15. A method according to embodiment 14, wherein the roughening of the two main surface portions is carried out by a blasting process or chemically.

16. A method according to embodiment 14, wherein the edge is masked to prevent roughening during the blasting or chemical treatment.

17. A method according to embodiment 14 or 15, wherein the edge is roughened during roughening of the main surface portions and subsequently polished after the roughening of the main surface portions to thereby obtain the process of roughening the surface portions without roughening the edge.

18. A method according to any of embodiments 14-17, wherein the edge is polished to obtain a first part having a first edge surface roughness and a second part having a second edge surface roughness being lower than the first edge surface roughness.

19. A method according to embodiment 18, wherein the first part of the edge is coated with the surface coating and the second part of the edge is uncoated.

20. A method according to embodiment 19, wherein the second part is shaped as at least one sharp corner of the edge between an edge part extending in the longitudinal direction and an edge part terminating the electrode in the distal end.

21. An electrosurgical pencil comprising an electrode according to any of embodiments 1-13.

The invention claimed is:

1. An electrode for an electrosurgical pencil, the electrode comprising:

an elongated body made of a conductive material and extending in an axial direction from a proximal end to a distal end, wherein the proximal end is configured for engaging the electrosurgical pencil, wherein the distal end forms a blade configured for cutting or coagulation of tissue by electrosurgical energy received from the electrosurgical pencil, wherein the blade is defined by two main surface portions on opposite sides of an intermediate plane and joined by an edge extending through the intermediate plane, wherein the edge comprises a smooth-part, and wherein the main surface portions have a first surface roughness, wherein the smooth-part of the edge has a second surface roughness being lower than the first surface roughness, wherein at least the main surface portions are covered by a surface coating, wherein the smooth-part of the edge is un-coated by the surface coating, and wherein the first surface roughness is in a range of 2.0 $R_a$ to 4.0 $R_a$, and the second surface roughness is less than 1.0 $R_a$.

2. The electrode according to claim 1, wherein the edge forms two axial edges extending in the axial direction, and one tip edge terminating the blade in the distal end, wherein the smooth-part is constituted by at least a part of the two axial edges, and wherein the tip edge has a larger roughness than the smooth-part.

3. The electrode according to claim 1, wherein the edge forms two axial edges extending in the axial direction, and one tip edge terminating the blade in the distal end, wherein the smooth-part is constituted by at least a part of the two axial edges and a part of the tip edge.

4. The electrode according to claim 1, wherein the surface coating has a friction which is lower than the friction of the smooth-part of the edge.

5. The electrode according to claim 1, wherein the surface coating comprises silicone.

6. The electrode according to claim 1, wherein the surface coating has a non-even coating thickness.

7. The electrode according to claim 1, wherein the second surface roughness is less than half of the first surface roughness.

8. The electrode according to claim 1, wherein the edge is at least partly un-covered by the surface coating.

9. The electrode according to claim 8, wherein a first part of the edge is covered by the surface coating and a second part of the edge is uncovered.

10. The electrode according to claim 9, wherein the second part of the edge is the smooth-part of the edge.

11. The electrode according to claim 9, wherein the first part has a first edge surface roughness and the second part has a second edge surface roughness, wherein the second edge surface roughness is lower than the first edge surface roughness.

12. The electrode according to claim 1, wherein the edge forms two axial edges extending in the axial direction, and one tip edge terminating the blade in the distal end, wherein a transition between each main surface portion and each axial edge forms an axial corner, wherein a transition between each main surface portion and the tip edge forms a tip corner, and wherein at least one of the tip corner and the axial corners are uncoated.

13. The electrode according to claim 1, wherein the edge forms two axial edges extending in the axial direction, and one tip edge terminating the blade in the distal end, wherein a transition between each main surface portion and each axial edge forms an axial corner, wherein a transition between each main surface portion and the tip edge forms a tip corner, and wherein the tip corner and the axial corners are uncoated.

14. The electrode of claim 1, wherein the two main surface portions have a surface area that is greater than a surface area of the edge.

15. A method of making an electrode for an electrosurgical pencil, the electrode comprising an elongated body made of a conductive material and extending in an axial direction from a proximal end to a distal end, the proximal end configured for engaging the electrosurgical pencil and the distal end forming a blade configured for cutting or coagulation of tissue by electrosurgical energy received from the electrosurgical pencil, the method comprising:

providing the elongated body with two main surface portions on opposite sides of an axially extending intermediate plane and joined by an edge extending through the intermediate plane;

roughening the two main surface portions to form a first surface roughness in a range of 2.0 $R_a$ to 4.0 $R_a$;

polishing at least a part of the edge to form a smooth-part having a second surface roughness less than 1.0 $R_a$; and coating at least the two main surface portions with a surface coating comprising silicone, wherein the smooth-part of the edge is un-coated by the surface coating.

16. The method according to claim 15, wherein the roughening of the two main surface portions is carried out by a blasting process or chemically.

17. The method of claim 15, wherein coating at least the two main surface portions comprises:

orienting a rod with a working area of the electrode pointing in a downwards direction relative to a direction of gravity;

dipping the working area in a liquid silicone polymer;

withdrawing the working area from the liquid silicone polymer;

after withdrawing the working area from the liquid silicone polymer, maintaining the rod in the downwards direction to allow the liquid silicone polymer to drip and mechanically removing the liquid silicone polymer from the edge;

after mechanically removing the liquid silicone polymer from the edge, inverting the electrode such that the working area is oriented in an upwards direction relative to the direction of gravity; and while inverting the electrode, curing the liquid silicone polymer.

18. The method of claim 15, wherein polishing the at least the part of the edge to form the smooth-part comprises polishing a first part of the edge and not polishing a second part of the edge to provide the first part with a first edge surface roughness and the second part with a second edge surface roughness, wherein the second edge surface roughness is lower than the first edge surface roughness.

19. The method of claim 18, further comprising coating the first part of the edge, wherein the second part of the edge is un-coated by the surface coating.

20. The method of claim 18, further comprising:

coating the first part of the edge and the second part of the edge with the surface coating; and polishing the second part of the edge to make the second part of the edge un-coated by the surface coating.

* * * * *